US007820111B2

(12) United States Patent
Brown

(10) Patent No.: US 7,820,111 B2
(45) Date of Patent: Oct. 26, 2010

(54) BLOOD SPECIMEN DISPENSER

(76) Inventor: Bradley V. Brown, 15059 Cedar St., Leawood, KS (US) 66224

( * ) Notice: Subject to any disclaimer, the term of this patent is extended or adjusted under 35 U.S.C. 154(b) by 309 days.

(21) Appl. No.: 12/228,592

(22) Filed: Aug. 14, 2008

(65) Prior Publication Data

US 2010/0041131 A1 Feb. 18, 2010

(51) Int. Cl.

| | |
|---|---|
| ***B01L 3/02*** | (2006.01) |
| ***G01N 15/06*** | (2006.01) |
| ***G01N 33/00*** | (2006.01) |
| ***G01N 33/48*** | (2006.01) |

(52) U.S. Cl. ....................... 422/100; 422/101; 422/102; 422/103; 436/63; 436/66; 436/71; 436/174; 436/177; 436/178; 436/180

(58) Field of Classification Search ................. 422/100, 422/101, 102, 103; 436/63, 66, 71, 174, 436/177, 178, 180

See application file for complete search history.

(56) References Cited

U.S. PATENT DOCUMENTS

| | | | | |
|---|---|---|---|---|
| 3,113,688 | A * | 12/1963 | Rasmussen | 73/864.03 |
| 4,210,156 | A * | 7/1980 | Bennett | 73/864.01 |
| 4,298,011 | A * | 11/1981 | Mangurten et al. | 600/576 |
| 5,110,557 | A | 5/1992 | Brown et al. | |
| 5,238,655 | A | 8/1993 | Laible et al. | |
| 5,269,317 | A * | 12/1993 | Bennett | 600/573 |
| 5,353,806 | A * | 10/1994 | Heinzelman et al. | 600/576 |

* cited by examiner

*Primary Examiner*—Brian J Sines
(74) *Attorney, Agent, or Firm*—Dennis L. Thomte; Thomte Patent Law Office LLC

(57) ABSTRACT

A blood specimen dispenser is provided which dispenses a precise amount of collected blood from a blood specimen collector onto filter paper or the like for screening or evaluation.

2 Claims, 5 Drawing Sheets

BLOOD SPECIMEN DISPENSER

BACKGROUND OF THE INVENTION

1. Field of the Invention

This invention relates to a blood specimen dispenser and more particularly to a blood specimen dispenser which is designed to dispense a precise amount of blood onto a spot of a filter paper or the like for the screening thereof.

2. Description of the Related Art

In U.S. Pat. Nos. 5,110,567 and 5,238,655, Applicant disclosed blood collection devices which collect blood from a puncture site of a patient to enable blood of patient, such as a newborn or older child, to be screened. Applicant previously described a Quick-Spot® Dispenser for newborn and pediatric screening in a promotional publication but the dispenser thereof was not placed into commercial production.

In Applicant's prior Quick-Spot® Dispenser, the blood in the blood collection device was collected in devices in such as that of the '567 and '655 patents and was then discharged therefrom onto a spot on a filter paper or the like for later screening and/or analysis. Since the filter paper of the prior art had circular spots or areas onto which the collected blood was to be placed, it was important that a precise amount of blood be placed within the circular spot on the filtered paper. In Applicant's earlier illustrated blood specimen dispenser, the blood was discharged from the blood collection vial by means of a conventional syringe but the proper amount of blood discharged therefrom was difficult to control since the plunger of the syringe had to be precisely depressed to discharge the proper amount of blood onto the spot of the filtered paper.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A blood specimen dispenser is disclosed comprising a blood specimen collector including a generally L-shaped body having a generally horizontally disposed body portion and a generally vertically disposed body portion extending generally upwardly from the horizontally disposed body portion. The vertically disposed body portion has a lower end and an upper end, and a hollow blood vial, having a closed door and an open upper end, is secured at its lower end to the upper end of the vertically disposed body portion. The vertically disposed body portion has a pick-up tube portion at its lower end with the pick-up tube having a first bore formed in the lower end which extends therethrough.

An elongated hollow drop tube extends upwardly from the upper end of the vertically disposed body portion into the blood vial. The drop tube has a lower end and an upper end with the upper end positioned below the upper end of the blood vial. The lower end of the drop tube is in fluid communication with the first bore in the pick-up tube portion. The L-shaped body has a second bore formed therein which extends through the horizontally extending portion and a third bore which extends through the vertically extending portion to the upper end of the vertically extending body portion. The second bore has an inlet opening and the third bore has an air discharge opening which is in communication with the interior of the blood vial. A first hydrophobic filter is positioned in the air discharge opening of the third bore.

A generally T-shaped check valve assembly is operatively connected to the blood specimen collector and comprises a first elongated hollow body portion having an air inlet end and an air discharge end. A second hollow body portion extends transversely from the first body portion intermediate the air inlet end and the air discharge end and is in communication with the interior of the first body portion. A first one-way check valve is provided in the first body portion between the air inlet end and the juncture of the second body portion and the first body portion. The first check-valve permits air to flow from the air inlet end of the check-valve assembly towards the air discharge end thereof and prevents air from passing therethrough towards the air inlet end of the check-valve assembly.

A second one-way check-valve is provided in the first body portion between the air discharge end of the first body portion and the juncture of the second body portion and the first body portion. The second check-valve permits air to flow therethrough towards the air discharge end of the first body portion while preventing air from passing therethrough from the air discharge end of the first body portion towards the air inlet end of the first body portion.

A volumetric pipetter is connected to the second body portion whereby the volumetric pipetter may be operated to force a predetermined amount of air into the first body portion between the first and second check valves and out of the air discharge end of the first body portion.

A second hydrophobic filter is positioned downstream of the air discharge end of the first body portion which permits air to flow therethrough while preventing blood to flow therethrough towards the second check valve. The air inlet of the second bore of the blood specimen dispenser is in communication with the downstream side of the second hydrophobic filter. The operation of the volumetric pipetter causes a predetermined volume of air to be discharged therefrom and passed through the second check valve, through the second hydrophobic filter, through the second bore in the L-shaped body, passed through the first hydrophobic filter and into the lower end of the blood vial thereby causing a predetermined volume of blood in the blood vial to be discharged therefrom into the upper end of the draw tube for discharge from the pick-up tube.

It is therefore a principal object to provide an improved blood specimen dispenser.

A further object of the invention is to provide an improved blood specimen dispenser which dispenses a precise amount of blood onto a spot on a filter paper for screening thereof.

A further object of the invention is to provide a blood specimen dispenser which prevents contamination of the blood specimen.

Still another object of the invention is to provide a blood specimen dispenser which dispenses precisely measured volumes of blood directly from the blood specimen dispenser onto a filter paper for analysis.

Still another object of the invention is to provide a blood specimen dispenser including a hydrophobic membrane disk filter which prevents foreign particles from entering the specimen container and to prevent blood from back-flowing into the valve assembly should the membrane in the dispenser fail.

Still another object of the invention is to provide a blood specimen dispenser which is used in combination with a blood specimen collector.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 4 is a perspective view illustrating the manner in which the blood specimen dispenser of this invention is used to place a blood specimen on a spot of a filter paper or the like.

DESCRIPTION OF THE PREFERRED EMBODIMENT

Figure 1:
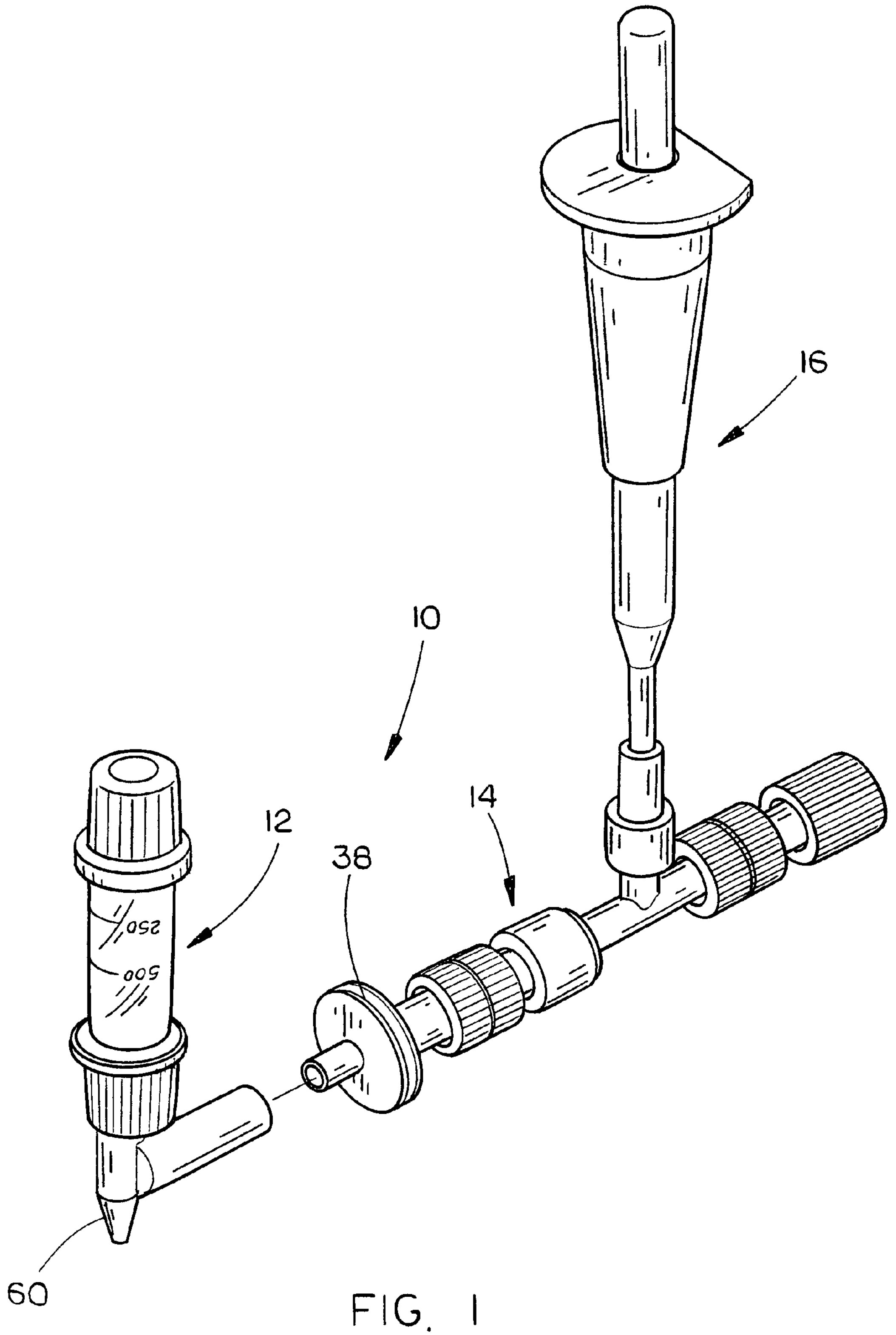
FIG. 1 is a perspective view of the blood specimen dispenser of this invention with the blood specimen collector being disconnected from the check-valve assembly and volumetric pipetter.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The blood specimen dispenser of this invention is referred to generally by the reference numeral 10 and generally includes a blood specimen collector 12 such as disclosed in U.S. Pat. Nos. 5,110,567 and 5,238,655, the disclosures of which are incorporated herein and are relied upon to complete the disclosure hereof. The blood specimen dispenser 10 also includes a check-valve assembly 14 and a conventional volumetric pipetter 16.

Pipetter 16 includes a barrel 18 having a manually movable plunger 20 mounted therein. When plunger 20 is depressed, a precise measured amount of air is discharged from the lower end 22 thereof. Check-valve assembly 14 includes a first body portion 26 having an air inlet end 28 and an air discharge end 30 and also includes a second body portion 32 extending transversely from the first body portion 26 and which is in communication with the interior of the first body portion 26.

A first one-way check-valve 34 is positioned in the first body portion 26 inwardly of the air inlet end 28 and is designed to permit air flow therethrough from the inlet end 28 towards the other end of the check-valve assembly 14 while preventing flow from the other end of check-valve assembly 14 outwardly through the air inlet end 28. The numeral 36 refers to a one-way check-valve enclosed in the T-shaped body 24 inwardly of the air discharge end 30 which is adapted to permit air to pass outwardly therethrough discharge end 30 but will prevent air from passing inwardly from the air discharge end 30 towards the other end of the check-valve assembly 14.

The numeral 38 refers to a hydrophobic disk filter which is positioned at the discharge end 30 of the body portion 26 which will permit air to flow therethrough but which will prevent blood or other foreign particles to pass therethrough towards the check-valve 36.

Figure 2:
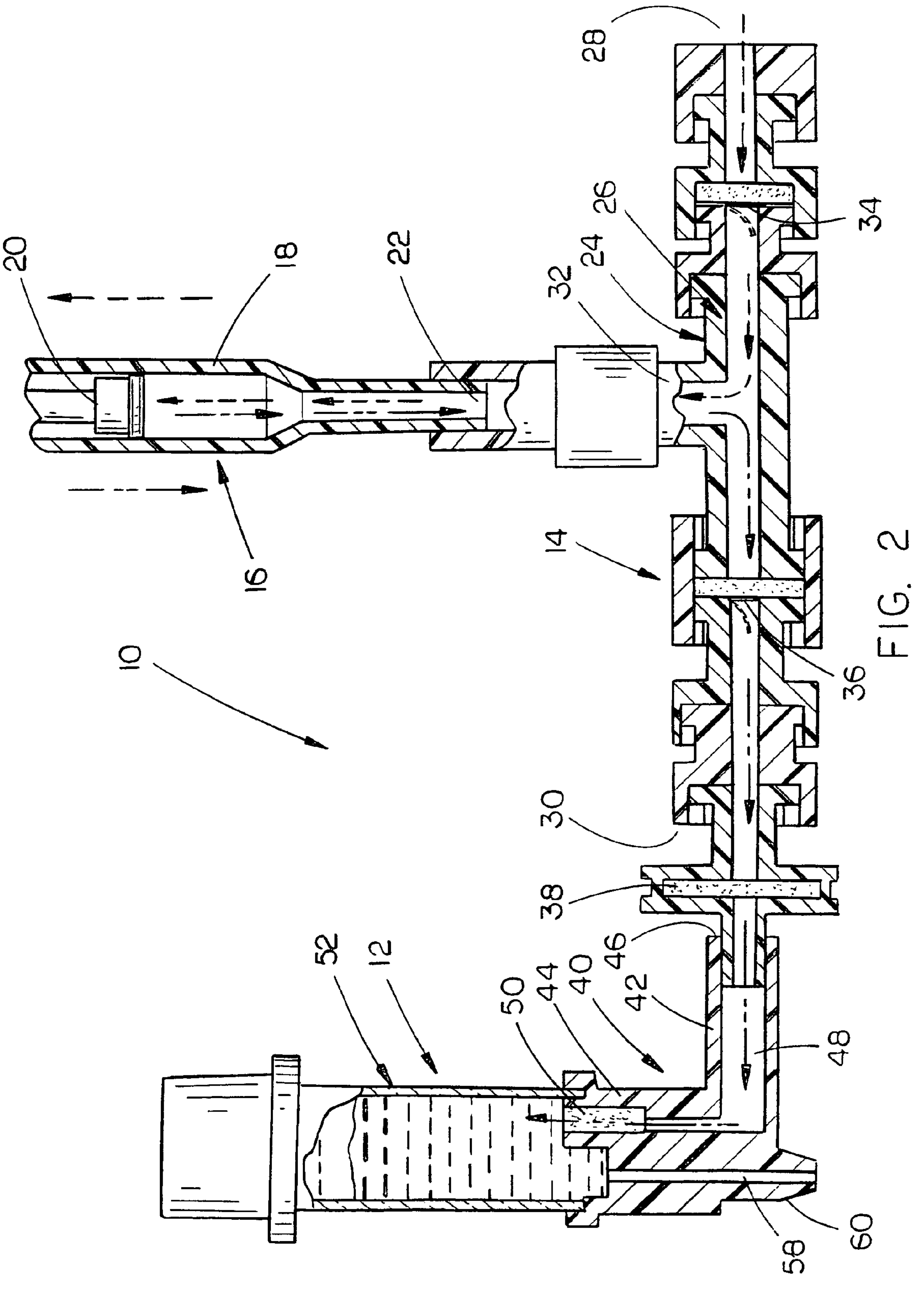
FIG. 2 is a sectional view of the structure shown in FIG. 1.
Figure 3:
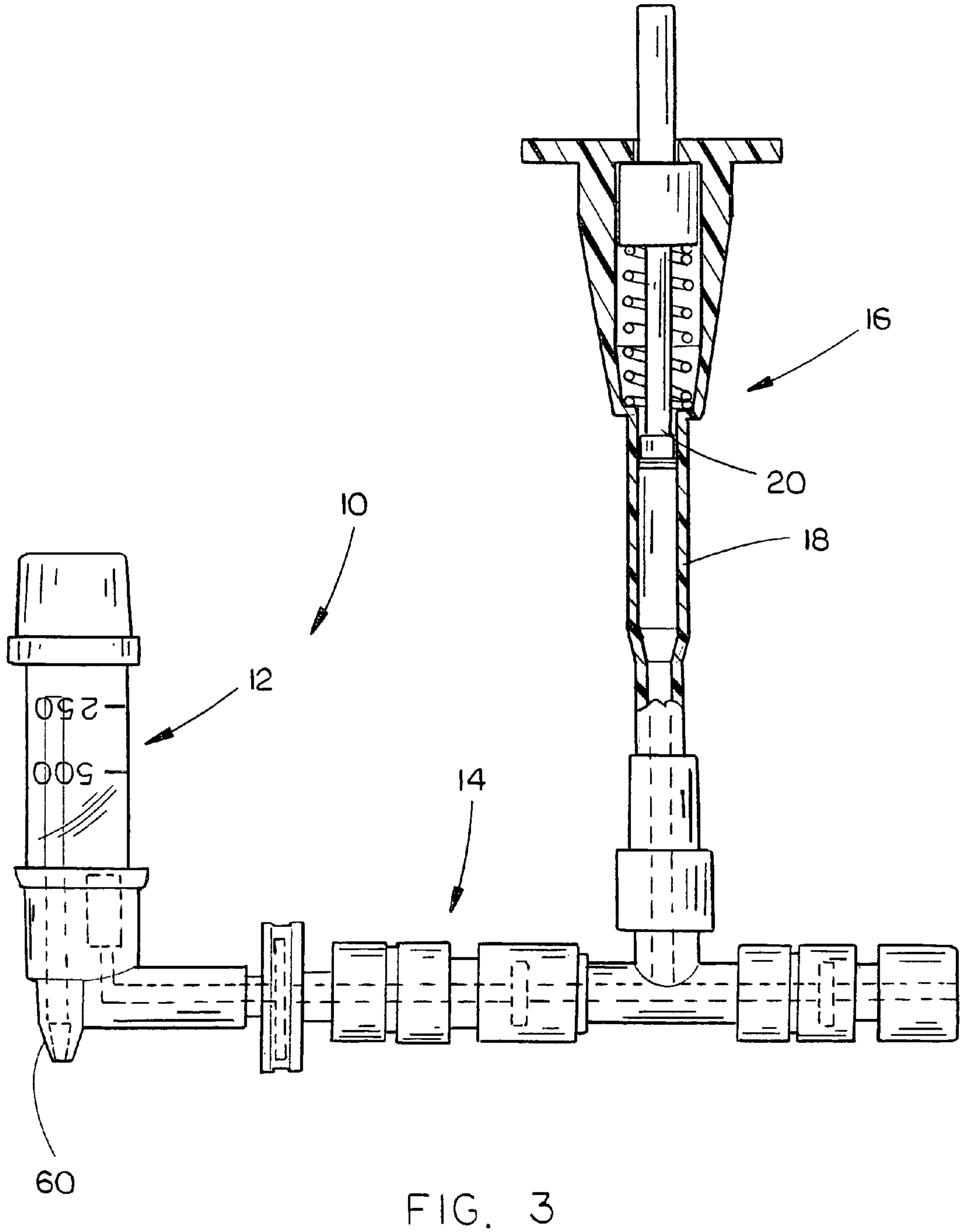
FIG. 3 is a side elevational view of the blood specimen dispenser of this invention with portions thereof cutaway to more fully illustrate the invention.

The specimen collector 12 includes a generally L-shaped body 40 including a generally horizontally disposed body portion 42 and a generally vertically disposed body portion 44. As seen in FIG. 2, the inlet end 46 of body portion 40 is in communication with the discharge end of the filter 38. Body 40 has a first bore 48 formed therein which extends from the inlet end 46 of the body portion 40 to the upper end of the body portion 44. The numeral 50 refers to a hydrophobic filter which is positioned in the upper end of the bore 48.

The numeral 52 refers to a blood vial having a closed upper end and a lower end which is secured to the upper end of body portion 44 as illustrated in FIG. 2. A bore 58 is formed in body 40 and extends from the lower end of the blood vial 52 to the lower end of the pick-up tube 60. The pick-up portion 60 picks blood up from the puncture site of a patient when blood is being collected within the vial 52 but which acts as a dispensing tip when used as a blood specimen dispenser.

Figure 4:
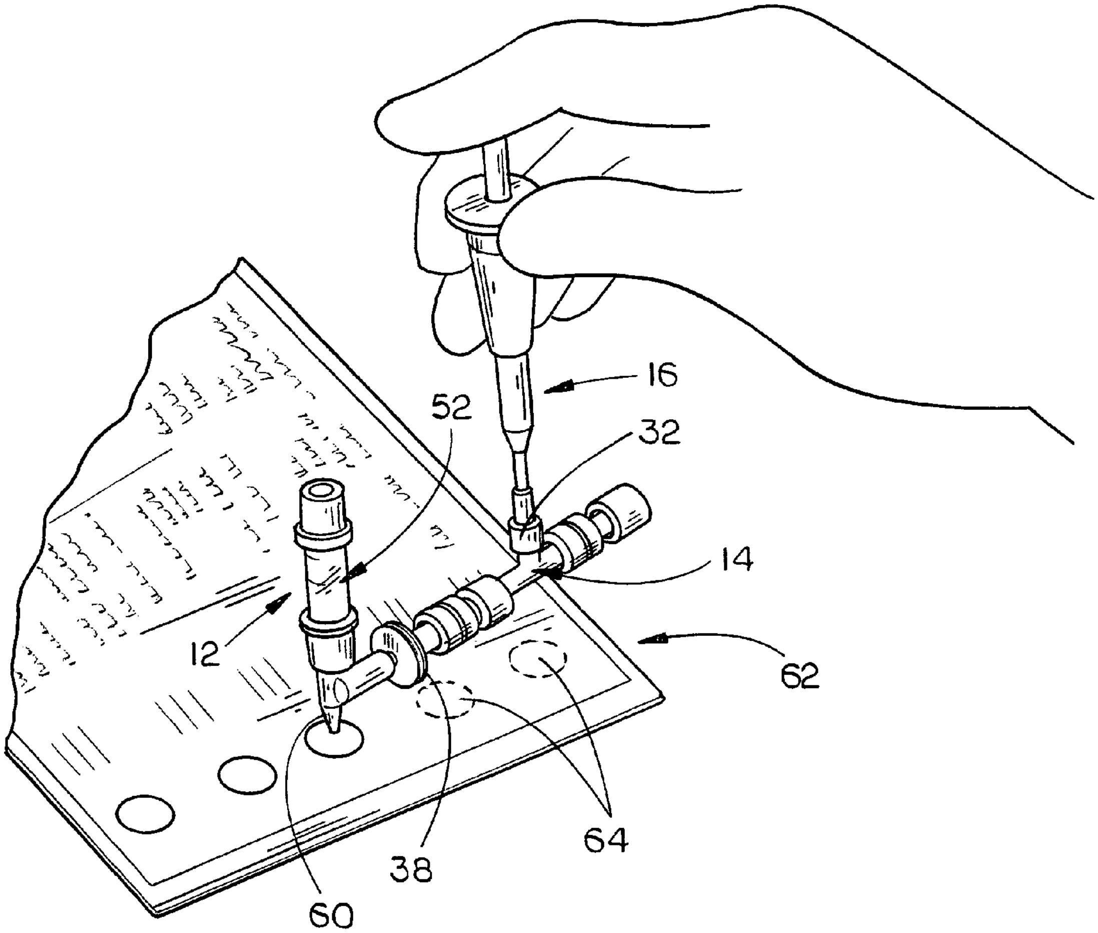

Referring to FIG. 4, the numeral 62 refers to a filter paper or the like having a plurality of spots 64 formed thereon onto which blood specimens will be placed as will be placed as will be described in more detail hereinafter.

Figure 5:
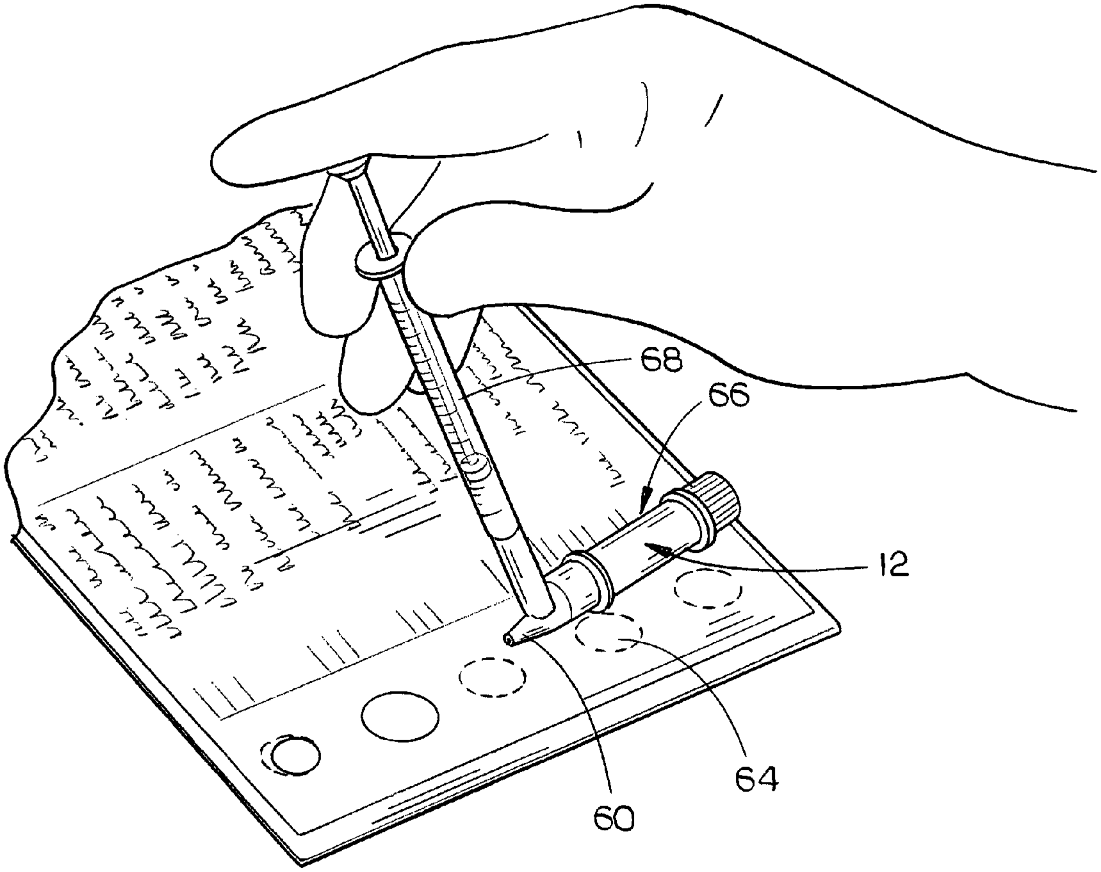
FIG. 5 (PRIOR ART)
FIG. 5 is a perspective view of Applicant's prior art blood specimen dispenser.

Referring to FIG. 5, the numeral 66 refers to Applicant's prior art blood specimen dispenser which included a blood specimen collector 12 having a pick-up tube 60 at one end thereof together with a syringe 68 coupled thereto for forcing blood from the collector 12 onto one of the spots 64. As previously stated, it was difficult to precisely control the amount of blood being dispensed from the dispenser thereof and it is for that reason that the invention of FIGS. 1-4 has been provided.

In use, after blood has been collected from a puncture site by the blood specimen collector 12, the collector 12 is secured to the outlet side of the hydrophobic filter. The pick-up tube 60 is then positioned over one of the spots 64 on the filter paper 62 and the volumetric pipetter 16 is fully depressed which causes a precise amount of air to be discharged therefrom and discharged into the check-valve assembly 14. The one-way check-valve 34 prevents air from being discharged from the pipetter 16 to pass outwardly of the check-valve assembly 14 but permits air to pass to the left through the check-valve assembly 36, through the hydrophobic filter 38, into bore 48, through hydrophobic filter 50 and into the interior of the vial 52. The air being introduced into the vial 52 will cause the blood therein to move downwardly so that a precise amount of blood will flow downwardly into the bore 58 and out of the pick-up tube 60. After the precise amount of blood has been placed on the spot 60, the plunger 20 of the pipetter 16 will be withdrawn so that air will be drawn upwardly thereinto the barrel 18 thereof through the inlet end 28 of the body portion 24, through the check-valve 34 and upwardly into the barrel 18. When the pick-up tube 60 has been placed over a second spot 64, the process will be repeated by depressing the plunger 20.

Thus it can be seen that a novel blood specimen dispenser has been provided which enables a precise and predetermined amount of blood to be dispensed therefrom so that a proper amount of blood will be placed on one of the spots 64 of the filter paper 62. The hydrophobic filters insure that blood or other contaminants may not enter the interior of the check-valve assembly 14 or the interior of the volumetric pipetter.

A very important feature of this invention is its ability to dispense consecutive drops without disconnecting the volumetric pipetter 16 from the specimen collector to allow air to refill the pipetter 16 for another dispensing. Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

The invention claimed is:

1. A blood specimen dispenser, comprising:

a blood specimen collector including a generally L-shaped body having a generally horizontally disposed body portion, and a generally vertically disposed body portion extending generally upwardly from said horizontally disposed body portion;

said vertically disposed body portion having a lower end and an open upper end;

a hollow blood vial having a closed upper end and an open lower end;

said lower end of said blood vial being secured to said upper end of said vertically disposed body portion;

said vertically disposed body portion having a pick-up tube portion at its said lower end;

said pick-up tube having a first bore formed therein which extends therethrough;

said lower end of said blood vial being in fluid communication with said first bore in said pick-up tube portion;

said L-shaped body having a second bore formed therein which extends through said horizontally extending portion and a third bore extending through said vertically extending portion to said upper end of said vertically extending body portion;

said second bore having an air inlet opening;

said third bore having an air discharge opening which is in communication with the interior of said blood vial;

a first hydrophobic filter positioned in said air discharge opening of said third bore;

a generally T-shaped check valve assembly comprising:

a first elongated hollow body portion having an air inlet end and a second air discharge end;

a second hollow body portion extending transversely from said first body portion intermediate said air inlet end and said air discharge end and being in communication with the interior of said first body portion;

a first one-way check valve in said first body portion between said air inlet end and the juncture of said second body portion and said first body portion;

said first check valve permitting air to flow from said air inlet end of said check valve assembly towards said air discharge end while preventing air from passing therethrough towards said air inlet end of said check valve assembly;

a second one-way check valve in said first body portion between said air discharge end of said first body portion and the juncture of said second body portion and said first body portion;

said second check valve permitting air to flow therethrough towards said air discharge end of said first body portion while preventing air from passing therethrough from said air discharge end of said first body portion towards said air inlet end of said first body portion;

a volumetric pipetter connected to said second body portion whereby said volumetric pipetter may be operated to force a predetermined volume of air into said first body portion between said first and second check valves and out of said air discharge end of said first body portion;

a second hydrophobic filter positioned downstream of said air discharge end of said first body portion which permits air to flow therethrough while preventing blood to flow therethrough towards said second check valve;

said air inlet of said second bore of said blood specimen dispenser being in communication with the downstream side of said second hydrophobic filter;

the operation of said volumetric pipetter causing a predetermined volume of air to be discharged therefrom and passed through said second check valve, passed through said second hydrophobic filter, passed through said second bore in L-shaped body, passed through said third bore in said L-shaped body and passed through said first hydrophobic filter and into the lower end of said blood vial thereby causing a predetermined volume of blood in said blood vial to be discharged therefrom into said first bore of said pick-up tube.

2. A blood specimen dispenser, comprising:

a blood specimen collector including a generally L-shaped body having a generally horizontally disposed body portion, and a generally vertically disposed body portion extending generally upwardly from said horizontally disposed body portion;

said vertically disposed body portion having a lower end and an open upper end;

a hollow blood vial having a closed upper end and an open lower end;

said lower end of said blood vial being secured to said upper end of said vertically disposed body portion;

said vertically disposed body portion having a pick-up tube portion at its said lower end;

said pick-up tube having a first bore formed therein which extends therethrough;

said lower end of said blood vial being in fluid communication with said first bore in said pick-up tube portion;

said L-shaped body having a second bore formed therein which extends through said horizontally extending portion and a third bore extending through said vertically extending portion to said upper end of said vertically extending body portion;

said second bore having an air inlet opening;

said third bore having an air discharge opening which is in communication with the interior of said blood vial;

a first hydrophobic filter positioned in said air discharge opening of said third bore;

a generally T-shaped check valve assembly comprising:

a first elongated hollow body portion having an air inlet end and a second air discharge end;

a second hollow body portion extending transversely from said first body portion intermediate said air inlet end and said air discharge end and being in communication with the interior of said first body portion;

a first one-way check valve in said first body portion between said air inlet end and the juncture of said second body portion and said first body portion;

said first check valve permitting air to flow from said air inlet end of said check valve assembly towards said air discharge end while preventing air from passing therethrough towards said air inlet end of said check valve assembly;

a second one-way check valve in said first body portion between said air discharge end of said first body portion and the juncture of said second body portion and said first body portion;

said second check valve permitting air to flow therethrough towards said air discharge end of said first body portion while preventing air from passing therethrough from said air discharge end of said first body portion towards said air inlet end of said first body portion;

a repeating volumetric pipetter connected to said second body portion whereby said repeating volumetric pipetter may be operated to force a predetermined volume of air into said first body portion between said first and second check valves and out of said air discharge end of said first body portion;

the operation of said repeating volumetric pipetter causing a predetermined volume of air to be discharged therefrom and passed through said second check valve, passed through said second bore in L-shaped body, passed through said third bore in said L-shaped body and passed through said first hydrophobic filter and into the lower end of said blood vial thereby causing a predetermined volume of blood in said blood vial to be discharged therefrom into said first bore of said pick-up tube.

* * * * *